United States Patent [19]

Paiocchi

[11] Patent Number: 5,589,598
[45] Date of Patent: Dec. 31, 1996

[54] PROCESS OF PURIFICATION OF 2,6-DIISOPROPYLPHENOL

[75] Inventor: Maurizio Paiocchi, Milan, Italy

[73] Assignee: Zambon Group S.p.A., Vicenza, Italy

[21] Appl. No.: 457,592

[22] Filed: Jun. 1, 1995

[30] Foreign Application Priority Data

Sep. 28, 1994 [IT] Italy .................. MI94A1969

[51] Int. Cl.⁶ .................. C07C 37/68
[52] U.S. Cl. .................. 568/756; 568/750
[58] Field of Search .................. 568/750, 756

[56] References Cited

U.S. PATENT DOCUMENTS 3,271,314  9/1966  Ecke et al. .................. 252/52
5,175,376  12/1992  Nieminen et al. .................. 568/781

FOREIGN PATENT DOCUMENTS 1472793  5/1977  United Kingdom .

OTHER PUBLICATIONS

The Merck Index, Eleventh Ed., No. 7847, p. 1245, 1989.

Primary Examiner—Samuel Barts
Attorney, Agent, or Firm—Watson Cole Stevens Davis, PLLC

[57] ABSTRACT

A process for the purification of 2,6-diisopropylphenol (Propofol) by transformation of the crude Propofol into its ester with a carboxylic or sulphonic acid, crystallization and hydrolysis, is described.

10 Claims, No Drawings

PROCESS OF PURIFICATION OF 2,6-DIISOPROPYLPHENOL

The present invention relates to a process for the purification of 2,6-diisopropylphenol and, more particularly, it relates to a process for the purification of 2,6-diisopropylphenol by its transformation into an ester with a carboxylic or sulphonic acid, crystallization and hydrolysis.

2,6-Diisopropylphenol is a compound known from some time as an antioxidant and as a chemical intermediate (U.S. Pat. No. 3,271,314 —Ethyl Corporation) and it is liquid at room temperature (m.p. 18° C.).

More recently its anaesthetic use by intravenous administration has been described in literature (British Patent No. 1.472,793 —Imperial Chemical Industries Limited).

2,6-Diisopropylphenol is a compound available on the market, generally prepared by Friedel-Crafts alkylation from phenol and propane. However, by this synthesis, 2,6-diisopropylphenol is obtained in mixture with not negligible amounts of by-products, mainly of position isomers.

In fact, 2,6-diisopropylphenol available on the market has a maximum purity degree of 97%.

It is clear that for the pharmaceutical use thereof, 2,6-diisopropylphenol, which will be referred herein after to as its International Nonproprietary Name Propofol (The Merck Index —XI Ed., No. 7847, page 1245), must have a very high purity degree, generally equal to or higher than 99%.

In U.S. Pat. No. 5,175,376 (Leiras Oy) it is shown that the purification of a commercially available Propofol could be carried out by fractional distillation but this is a very difficult and long process due to the small differences between the boiling point of Propofol and that of its isomers.

In any case, even if very efficient equipments are used it is not possible to obtain a product with a satisfactory purity degree.

In order to avoid this inconvenient, in said patent, a process for the purification of Propofol is disclosed which relates to the fractional distillation of the commercial product up to obtain a purity degree of 99.7% and to the subsequent crystallization with or without solvent at a temperature lower than the melting point of Propofol, preferably between −20° C. and −10° C.

To the best of our knowledge, no other method for the purification of Propofol which allows to obtain a product with a purity degree suitable for the pharmaceutical use has been described in literature.

We have now found and it is the object of the present invention a process for the purification of Propofol which comprises the transformation of the crude Propofol into an ester solid at room temperature of formula

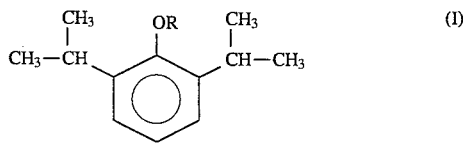

wherein R is a residue of a carboxylic or sulphonic acid, the crystallization of the ester (I) in order to obtain a purity degree equal to or higher than 99.9% and the subsequent hydrolysis.

The obtained Propofol has a purity degree suitable for the use in the pharmaceutical field.

With the term crude Propofol we intend a commercially available Propofol having a purity degree generally equal to or lower than 97%.

The carboxylic or sulphonic acid useful for the preparation of the ester (I) is a carboxylic or sulphonic acid able to transform Propofol into an ester solid at room temperature, such as an optionally substituted benzoic acid, a $C_1$–$C_3$ alkylsulphonic acid or an aryl-sulphonic acid that is an optionally substituted phenyl- or naph- thyl-sulphonic acid.

Specific examples of substituted benzoic acids are p.methoxybenzoic acid, p.chlorobenzoic acid and p.nitrobenzoic acid.

Specific examples of $C_1$–$C_3$ alkylsulphonic acid and of arylsulphonic acid are methanesulphonic acid, p.toluenesulphonic acid, benzenesulphonic acid and 1-naphthalenesulphonic acid.

Preferably benzoic acid and p.toluenesulphonic acid are used.

For the preparation of ester (I), the carboxylic or sulphonic acid is generally used as acyl halide, preferably as chloride.

The reaction is carried out according to conventional techniques in the presence of a base, such as triethylamine, in a suitable organic solvent such as methylene chloride, toluene, acetone or tetrahydrofuran.

The obtained ester (I) is directly crystallized to obtain product (I) with a purity equal to or higher than 99.9%.

It is evident to the man skilled in the art that, especially when the starting crude Propofol has a purity degree particularly low, it might be necessary to carry out more than one crystallization in order to obtain ester (I) with the desired purity.

In any case, a crystallization is a simple and rather cheap industrial operation.

Suitable crystallization solvents are lower alcohols such as methanol, ethanol, propanol, isopropanol, n.butanol, isobutanol, sec.butanol, tert.butanol.

Particularly preferred are methanol, isopropanol and sec.butanol. The subsequent hydrolysis is carried out by heating ester (I) in a suitable organic solvent in the presence of a base, preferably an aqueous alkaline hydroxide such as, for example, sodium or potassium hydroxide.

Suitable solvents are methanol, isopropanol and dimethylsulphoxide. The hydrolysis allows to obtain Propofol in high yields and high purity. In fact, the obtained Propofol does not need further purifications and is distilled off, according to conventional techniques, by obtaining a single pure fraction.

In a practical embodiment the purification process object of the present invention is carried out as follows.

Crude Propofol having a purity of about 97% is treated with a carboxylic or sulphonic acid chloride in the presence of a base in a suitable organic solvent.

The resultant crude solid ester (I) is directly crystallized one or more times in a suitable solvent by obtaining the product with a purity equal to or higher than 99.9%.

The obtained pure ester (I) is then hydrolyzed to Propofol by heating in a suitable solvent in the presence of an aqueous alkaline hydroxide.

After separation of the phases and evaporation of the organic solvent under reduced pressure, the residue is distilled under vacuum to completely remove possible traces of the solvent thus obtaining Propofol with purity equal to or higher than 99.9% in a single pure fraction.

The process object of the present invention allows to purify Propofol by obtaining a product with a purity degree suitable for the pharmaceutical use.

The purification does not need unusual operative conditions, such as crystallization at low temperatures, or particularly burdensome operations such as repeated fractional distillations.

Even if it requests an esterification, a crystallization and a hydrolysis, the process has a very high global yield, surely higher than that of other known purification processes.

Furthermore, the possibility to carry out more than one crystallization of ester (I) allows to obtain Propofol with desired purity and with high yields also starting from a very impure crude product.

With the aim to better illustrate the present invention the following examples are now given.

In the examples the following abbreviation has been used: GLC=gas-liquid chromatography

EXAMPLE 1

Preparation of 2,6-diisopropylphenyl benzoate

Triethylamine (217 g; 2.15 mol) was added to a mixture of 2,6-diisopropylphenol (356 g; 2 mol; 97% purity) in methylene chloride (600 ml), by keeping the temperature at 20°±5° C.

Benzoyl chloride (295 g; 2.1 mol) was added dropwise to the solution kept under stirring, without exceeding the temperature of 25° C.

At the end of the addition, the mixture was kept under stirring for 4 hours.

After addition of water (500 ml), the phases were separated.

The organic phase was washed with water (500 ml) and concentrated to residue under vacuum.

Methanol (1000 ml) was added to the residue and the mixture was heated to reflux.

After cooling at 20° C. in 1 hour, the suspension was cooled to 0°–5° C. for 1 hour.

The precipitate was filtered off and washed with cool (about 0° C.) methanol (2×100 ml).

After drying under vacuum at 40° C. up to constant weight, 2,6-diisopropylphenyl benzoate (493 g; 1.75 mol) was obtained.
87.4% yield.
GLC purity >99.9%
M.p. 80°–81° C.

EXAMPLE 2

Preparation of 2,6-diisopropylphenl

A mixture of 2,6-diisopropylphenyl benzoate (450 g; 1.6 mol) in methanol (800 ml), kept under nitrogen, was heated to 58° C.±2° C. up to afford a solution.

A solution of 21.5% sodium hydroxide in water (480 g; 2.58 mol), was added to the solution in about 1 hour, by keeping the temperature at 60°±2° C.

The solution was kept at this temperature and under stirring for 3 hours (complete hydrolysis by GLC control).

The mixture was cooled to 30°–35° C. and a part of methanol was evaporated under vacuum.

After addition of water (2000 ml) and methylene chloride (300 ml), the phases were separated and the aqueous phase was extracted with methylene chloride (200 ml).

The collected organic phases were washed twice with water (200 ml). The organic phase was concentrated to residue under vacuum.

The resultant crude (278.5 g) was distilled under vacuum by obtaining pure 2,6-diisopropylphenol (260 g) (GLC purity>99.9%).

EXAMPLE 3

Preparation of 2,6-diisopropylphenol

Water (54 g; 3 mol) was added in about 0.5 hours to a mixture formed by 85% potassium hydroxide in flakes (66 g; 1 mole) and 2,6-diisopropylphenyl benzoate (141 g; 0.5 mol) in dimethylsulphoxide (140 ml), kept under nitrogen.

During the addition the temperature rised to 80°±2° C.

The solution was kept at 60° C. under stirring for 1 hour (complete hydrolysis by GLC control).

After addition of water (600 ml) and toluene (150 ml), the phases were separated and the aqueous phase further extracted with toluene (50 ml).

The collected organic phases were washed twice with water (100 ml).

The organic phase was concentrated to residue under vacuum.

The resultant crude (84 g) was distilled under vacuum by obtaining pure 2,6-diisopropylphenol (79 g) (GLC purity >99.9%).

EXAMPLE 4

Preparation of 2,6-diisopropylphenyl benzoate

Triethylamine (217 g; 2.15 mol) was added to a mixture of 2,6-diisopropylphenol (356 g; 2 mol; 97% purity) in methylene chloride (600 ml), by keeping the temperature at 20°±5° C.

Benzoyl chloride (295 g; 2.1 mol) was added dropwise to the solution kept under stirring, without exceeding the temperature of 25° C.

At the end of the addition, the mixture was kept under stirring for 4 hours.

After addition of water (500 ml), the phases were separated.

The organic phase was washed with water (500 ml) and concentrated to residue under vacuum.

Sec.butanol (1250 ml) was added to the residue and the mixture was heated to 60° C. up to obtaining a solution.

After cooling at 20° C. in 1 hour, the suspension was cooled to 0°–5° C. for 1 hour.

The precipitate was filtered off and washed with cool (about 0° C.) sec.butanol (2×100 ml).

After drying under vacuum at 40° C. up to constant weight, 2,6-diisopropylphenyl benzoate (440 g; 1.56 mol) was obtained.
78% yield.
GLC purity>99.9%
M.p. 80°–81° C.

EXAMPLE 5

Preparation of 2,6-diisopropylphenyl 4-methylphenylsulphonate

Triethylamine (22.2 g; 0.22 mol) was added to a mixture of 2,6-diisopropylphenol (35.6 g; 0.2 mol; 97% purity) in methylene chloride (70 ml), by keeping the temperature at 20°±5° C.

4-Methylphenylsulphonyl chloride (41 g; 0.215 mol) was added portionwise in 30 minutes to the stirred solution, kept under stirring. At the end of the addition, the mixture was kept under stirring at 20° C. for 2 hours.

After addition of water (100 ml), the phases were separated and the organic phase was concentrated to residue under vacuum.

Isopropanol (100 ml) was added to the residue and the mixture was heated to reflux.

After cooling at 20° C. in 1 hour, the suspension was cooled to 0°–5° C. for 1 hour.

The precipitate was filtered off and washed with cool (about 0° C.) isopropanol (2×100 ml).

After drying under vacuum at 40° C. up to constant weight, 2,6-diisopropylphenyl 4-methylphenylsulphonate (43.5 g; 0.13 mol) was obtained.
66% yield.
GLC purity>99.9%

EXAMPLE 6

Preparation of 2,6-diisopropylphenol

Water (27 g; 1.5 mol) was added in about 0.5 hours to a mixture formed by 85% potassium hydroxide in flakes (33 g; 0.5 mol) and 2,6-diisopropylphenyl 4-methylphenylsulphonate (83 g; 0.25 mol) in dimethylsulphoxide (70 ml), kept under nitrogen.

During the addition the temperature raised to 60° C.

The mixture was kept at 70° C. under stirring for 6 hours (complete hydrolysis by GLC control).

After addition of water (500 ml) and methylene chloride (150 ml), the phases were separated and the aqueous phase further extracted with methylene chloride (50 ml).

The collected organic phases were concentrated to residue under vacuum.

The resultant crude (50 g) was distilled under vacuum by obtaining pure 2,6-diisopropylphenol (40 g) (GLC purity>99.9%).

What we claim is:

1. A process for the purification of Propofol comprising the transformation of the crude Propofol into an ester solid at room temperature of formula

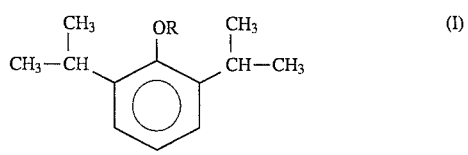

wherein R is a residue of a carboxylic or sulphonic acid, the crystallization of the ester (I) in order to obtain a purity degree equal to or higher than 99.9% and its subsequent hydrolysis.

2. A process according to claim 1 wherein the carboxylic or sulphonic acid is an optionally substituted benzoic acid, a $C_1$–$C_3$ alkylsulphonic acid or an arylsulphonic acid.

3. A process according to claim 1 wherein the carboxylic acid is benzoic acid, p-methoxybenzoic acid, p,chlorobenzoic acid or p.nitrobenzoic acid.

4. A process according to claim 1 or wherein the sulphonic acid is methanesulphonic acid, p-toluenesulphonic acid, benzenesulphonic acid or 1-naphthalenesulphonic acid.

5. A process according to claim 1 wherein the transformation of crude Propofol into its ester (I) is carried out by reacting it with the carboxylic or sulphonic acid in the form of acyl halide, in the presence of a base and in a suitable organic solvent.

6. A process according to claim 1 wherein the crystallization is carried out by using as solvent a lower alcohol.

7. A process according to claim 6 wherein the lower alcohol is methanol, ethanol, propanol, isopropanol, n-butanol, isobutanol, sec-butanol and tert-butanol.

8. A process according to claim 6 wherein the lower alcohol is methanol, isopropanol or sec-butanol.

9. A process according to claim 1 wherein the hydrolysis is carried out by heating the ester (I) in a suitable organic solvent in the presence of a base.

10. A process according to claim 9 wherein the suitable solvent is methanol, isopropanol or dimethylsulphoxide and the base is sodium or potassium hydroxide.

* * * * *